(12) United States Patent
Offutt (10) Patent No.: US 11,369,163 B1
(45) Date of Patent: Jun. 28, 2022

(54) ATHLETIC SHOE HAVING INTEGRAL ANKLE SUPPORT

(71) Applicant: Jesse Offutt, McCook, NE (US)

(72) Inventor: Jesse Offutt, McCook, NE (US)

( * ) Notice: Subject to any disclaimer, the term of this patent is extended or adjusted under 35 U.S.C. 154(b) by 343 days.

(21) Appl. No.: 16/701,262

(22) Filed: Dec. 3, 2019

(51) Int. Cl.
*A43B 7/20* (2006.01)
*A61F 5/01* (2006.01)
*A43B 5/00* (2022.01)

(52) U.S. Cl.
CPC ............. *A43B 7/20* (2013.01); *A61F 5/0111* (2013.01); *A43B 5/00* (2013.01)

(58) Field of Classification Search
CPC .... A43B 7/20; A43B 7/00; A43B 7/14; A43B 7/18; A43B 5/00; A61F 5/01; A61F 5/0111
See application file for complete search history.

(56) References Cited

U.S. PATENT DOCUMENTS

| | | | | |
|---|---|---|---|---|
| 3,381,173 A * | 4/1968 | De Woskin | ............ | A43B 3/163 361/223 |
| 4,517,968 A * | 5/1985 | Greene | ................ | A61F 5/0127 602/16 |
| 4,651,726 A * | 3/1987 | Holland | ................ | A61F 5/0111 602/65 |
| 4,936,295 A * | 6/1990 | Crane | .................... | A61F 5/0111 36/89 |
| 5,078,128 A * | 1/1992 | Grim | .................... | A61F 5/0127 602/23 |
| 5,094,232 A * | 3/1992 | Harris | ...................... | A43B 7/20 602/16 |
| 5,217,431 A * | 6/1993 | Toronto | ................ | A61F 5/0111 602/27 |
| 5,226,875 A * | 7/1993 | Johnson | ................ | A61F 5/0111 36/114 |
| 5,329,705 A * | 7/1994 | Grim | .................... | A43B 1/0009 36/110 |
| 5,368,551 A * | 11/1994 | Zuckerman | ........... | A61F 5/0111 602/23 |
| 5,378,223 A * | 1/1995 | Grim | .................... | A43B 5/0407 128/DIG. 20 |
| 5,429,588 A * | 7/1995 | Young | .................... | A61F 5/0127 36/28 |
| 5,464,385 A * | 11/1995 | Grim | .................... | A61F 5/0127 602/23 |

(Continued)

FOREIGN PATENT DOCUMENTS

WO 2013169308 11/2013

*Primary Examiner* — Shaun R Hurley
*Assistant Examiner* — Bao-Thieu L Nguyen
(74) *Attorney, Agent, or Firm* — Kyle A. Fletcher, Esq.

(57) ABSTRACT

The athletic shoe having integral ankle support is an item of footwear. The athletic shoe having integral ankle support is adapted for use with a foot. The athletic shoe having integral ankle prevents the ankle of the foot causing the foot to form a cant in the athletic shoe having integral ankle. The athletic shoe having integral ankle support comprises a base footwear, an ankle structure, and a sleeve structure. The ankle structure and the sleeve structure attach to the base footwear. The ankle structure forms the support structure that stabilizes the ankle. The sleeve structure is a tubular textile that forms a protective shell that protects the foot from injury by the ankle support structure.

19 Claims, 4 Drawing Sheets

(56) References Cited

U.S. PATENT DOCUMENTS

| | | | |
|---|---|---|---|
| 5,620,411 A * | 4/1997 | Schumann | A61F 5/0111 128/882 |
| 5,672,156 A * | 9/1997 | Jimenez Ramos | A43B 7/20 36/89 |
| 5,761,834 A * | 6/1998 | Grim | A43B 1/0009 36/110 |
| 5,775,008 A | 7/1998 | Bussell | |
| 5,792,087 A * | 8/1998 | Pringle | A61F 5/0127 602/23 |
| 6,652,474 B1 * | 11/2003 | Quinn | A61F 5/0111 128/882 |
| 6,792,700 B2 | 9/2004 | Gallegos | |
| 6,976,972 B2 * | 12/2005 | Bradshaw | A61F 5/0111 128/882 |
| 7,112,182 B1 * | 9/2006 | Zahiri | A61F 5/0111 128/882 |
| 8,622,947 B2 * | 1/2014 | Weaver, II | A61F 5/0111 602/27 |
| 8,776,402 B2 | 7/2014 | Cromer, Jr. | |
| 9,532,625 B2 | 1/2017 | Katz | |
| 11,026,473 B2 * | 6/2021 | Berns | A61F 5/0127 |
| 2004/0088887 A1 * | 5/2004 | Kim | A43B 7/20 36/89 |
| 2004/0111923 A1 * | 6/2004 | Brooks | A43B 23/07 36/89 |
| 2005/0054962 A1 * | 3/2005 | Bradshaw | A61F 5/0111 602/27 |
| 2005/0131324 A1 * | 6/2005 | Bledsoe | A61F 5/0111 602/23 |
| 2005/0145256 A1 * | 7/2005 | Howard | A61F 5/0111 128/882 |
| 2005/0222531 A1 * | 10/2005 | Moore | A61F 5/0111 602/27 |
| 2006/0004311 A1 * | 1/2006 | Hargrave | A61F 5/0111 602/5 |
| 2007/0113427 A1 | 5/2007 | Mansfield | |
| 2010/0036306 A1 * | 2/2010 | Lussier | A61F 5/0111 602/65 |
| 2010/0100018 A1 * | 4/2010 | Fout | A61F 5/0111 602/13 |
| 2010/0100020 A1 * | 4/2010 | Fout | A61F 5/0111 602/23 |
| 2011/0225846 A1 * | 9/2011 | Norton | A43C 11/1493 36/89 |
| 2012/0035520 A1 * | 2/2012 | Ingimundarson | A61F 5/0195 602/23 |
| 2012/0116275 A1 * | 5/2012 | Pochatko | A61F 5/0111 602/13 |
| 2014/0005585 A1 * | 1/2014 | Berns | A43B 7/20 602/27 |
| 2014/0115928 A1 * | 5/2014 | Pelletier, Jr. | A43B 5/04 36/116 |
| 2014/0196317 A1 | 7/2014 | Katz | |
| 2014/0276316 A1 * | 9/2014 | Bradshaw | A61F 5/0102 602/27 |
| 2014/0309572 A1 * | 10/2014 | Heyd | A61F 5/0111 602/27 |
| 2016/0000174 A1 * | 1/2016 | Grim | A43B 7/20 36/97 |
| 2016/0045353 A1 * | 2/2016 | Nayfa | A43B 7/20 602/16 |
| 2016/0213506 A1 * | 7/2016 | Chen | A61F 5/0195 |
| 2016/0235573 A1 * | 8/2016 | Walborn | A61B 5/1118 |
| 2016/0324676 A1 * | 11/2016 | Anderson | A61F 5/0111 |
| 2017/0165093 A1 * | 6/2017 | Huttenlocker | A61F 5/0111 |
| 2017/0273814 A1 * | 9/2017 | Berns | A43B 7/20 |
| 2017/0296373 A1 * | 10/2017 | Bean | A61F 5/0127 |
| 2018/0140450 A1 * | 5/2018 | Danek | A61F 5/0111 |
| 2018/0140452 A1 * | 5/2018 | Danek | A61F 5/0127 |
| 2018/0228634 A1 * | 8/2018 | Wang | A61F 5/0111 |
| 2019/0240057 A1 * | 8/2019 | Gunnsteinsson | A61F 5/0111 |
| 2019/0254853 A1 * | 8/2019 | Gildersleeve | A61F 5/0111 |
| 2019/0262159 A1 * | 8/2019 | Curran | A61F 5/0127 |
| 2019/0314185 A1 * | 10/2019 | Yuge | A61H 3/00 |
| 2019/0374362 A1 * | 12/2019 | Anderson | A61F 5/0111 |
| 2020/0093625 A1 * | 3/2020 | Hanft | A61F 5/0111 |
| 2020/0100928 A1 * | 4/2020 | Best | A61F 5/0111 |
| 2020/0100929 A1 * | 4/2020 | Best | A61F 5/0127 |
| 2020/0163789 A1 * | 5/2020 | Tsunoda | A61F 13/06 |
| 2020/0352780 A1 * | 11/2020 | Katz | A61F 7/02 |
| 2020/0360170 A1 * | 11/2020 | Giuntoli | A61F 5/012 |
| 2021/0259365 A1 * | 8/2021 | Maselino | A43C 11/14 |
| 2021/0259868 A1 * | 8/2021 | Aoki | A43B 7/20 |

* cited by examiner

ATHLETIC SHOE HAVING INTEGRAL ANKLE SUPPORT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of footwear including footwear with foot supporting parts, more specifically, footwear with a support that prevents the foot from canting to one side. (A43B7/04)

While footwear comes in many styles and forms, most commonly available footwear shares certain common characteristics including, but not limited to, an upper and a sole. The upper and sole are generally said to be attached at the feather. If the feather is reinforced with an additional piece of material, the additional piece of material is referred to as a welt. The upper is divided into a quarter regions and a vamp region. The superior edge of the upper is called the top line (or collar). A foot typically enters footwear through the topline. The quarter region covers the heel of the foot. The vamp region covers the toes and attaches to the quarter. The sole forms a pedestal between the foot and the ground. The sole is further defined with an insole and an outsole. The insole is the surface of the sole that is proximal to the foot when the footwear is worn normally. The outsole is the surface of the sole that is distal from the insole. The sole is often fitted with a heel which is a structure that is designed to raise the quarter portion of the footwear above the vamp. The tongue is a flap of material that is attached to the upper such that the tongue is positioned between a foot and the upper. The tongue is attached to the upper at the frenulum.

SUMMARY OF INVENTION

The athletic shoe having integral ankle support is an item of footwear. The athletic shoe having integral ankle support is adapted for use with a foot. The athletic shoe having integral ankle prevents the ankle of the foot causing the foot to form a cant in the athletic shoe having integral ankle. The athletic shoe having integral ankle support comprises a base footwear, an ankle structure, and a sleeve structure. The ankle structure and the sleeve structure attach to the base footwear. The ankle structure forms the support structure that stabilizes the ankle. The sleeve structure is a tubular textile that forms a protective shell that protects the foot from injury by the ankle support structure.

These together with additional objects, features and advantages of the athletic shoe having integral ankle support will be readily apparent to those of ordinary skill in the art upon reading the following detailed description of the presently preferred, but nonetheless illustrative, embodiments when taken in conjunction with the accompanying drawings.

In this respect, before explaining the current embodiments of the athletic shoe having integral ankle support in detail, it is to be understood that the athletic shoe having integral ankle support is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the athletic shoe having integral ankle support.

It is therefore important that the claims be regarded as including such equivalent construction insofar as they do not depart from the spirit and scope of the athletic shoe having integral ankle support. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
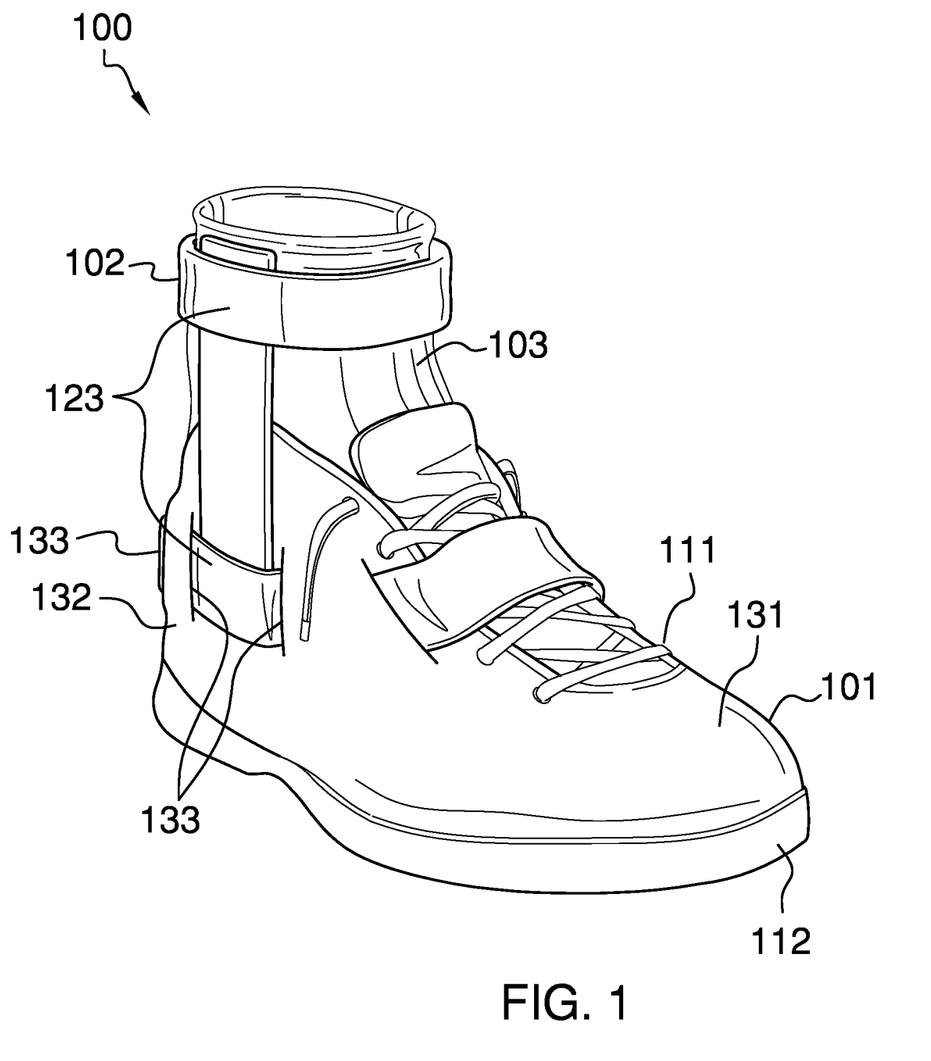
FIG. 1 is a perspective view of an embodiment of the disclosure.
Figure 2:
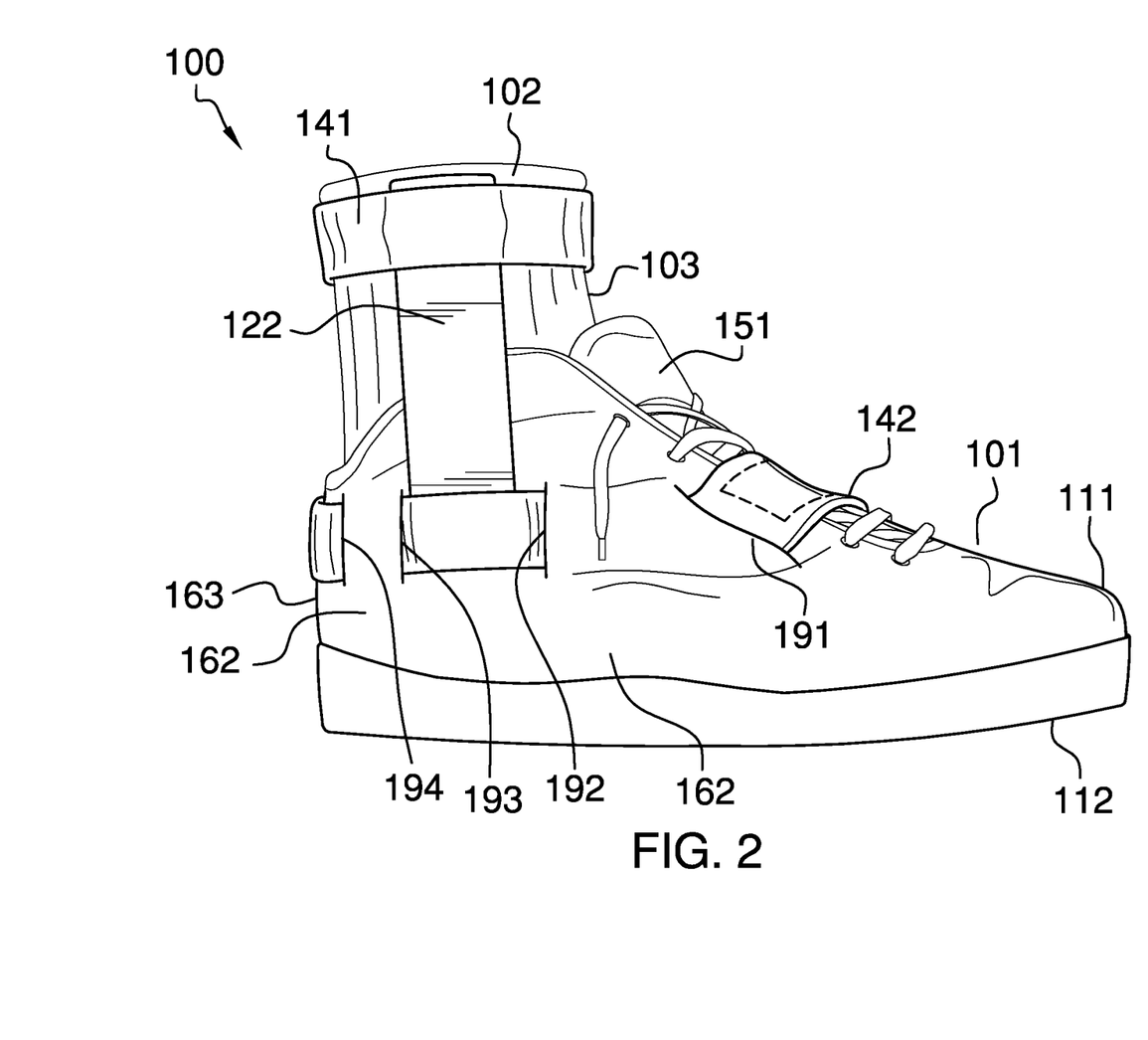
FIG. 2 is a side view of an embodiment of the disclosure.
Figure 3:
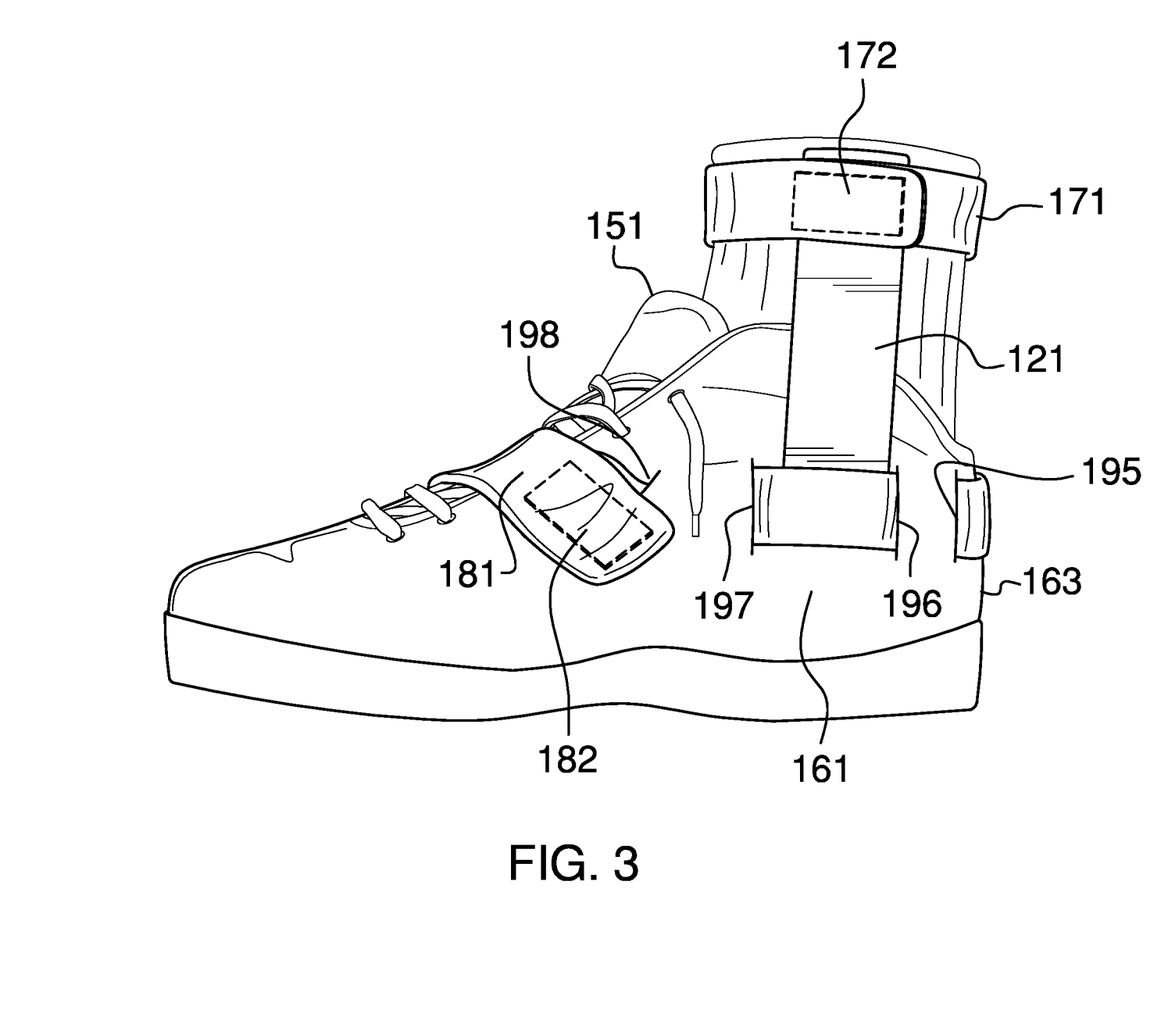
FIG. 3 is a reverse side view of an embodiment of the disclosure.
Figure 4:
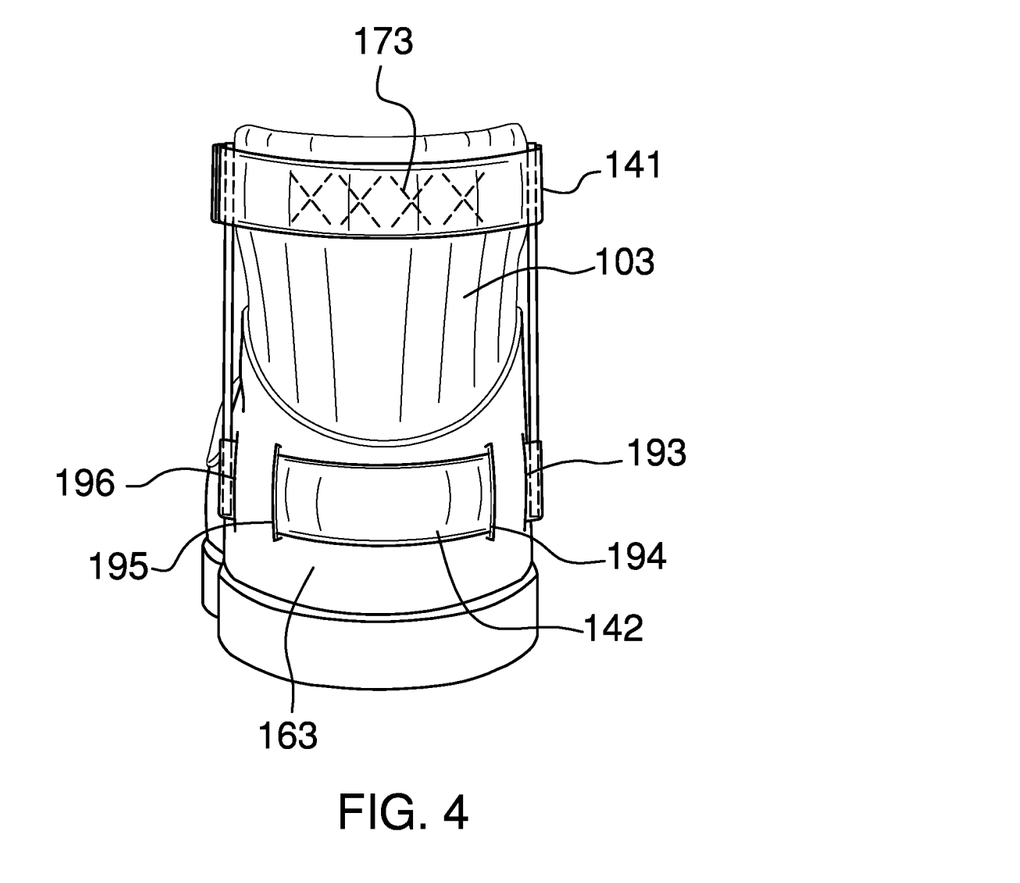
FIG. 4 is a rear view of an embodiment of the disclosure.

Detailed reference will now be made to one or more potential embodiments of the disclosure, which are illustrated in FIGS. 1 through 4.

The athletic shoe having integral ankle support 100 (hereinafter invention) is an item of footwear. The invention 100 is adapted for use with a foot. The athletic shoe having integral ankle prevents the ankle of the foot causing the foot to form a cant in the invention 100. The invention 100 comprises a base footwear 101, an ankle support structure 102, and a sleeve structure 103. The ankle support structure 102 and the sleeve structure 103 attach to the base footwear 101. The ankle support structure 102 forms the support structure that stabilizes the ankle. The sleeve structure 103 is a tubular textile that forms a protective shell that protects the foot from injury by the ankle support structure 102.

The base footwear 101 is an athletic shoe. The base footwear 101 is adapted to be worn on a foot. The base footwear 101 is adapted for used by an individual who is performing foot movements requiring rapid changes of direction. The use of the base footwear 101 is well-known and documented in the apparel and athletic arts. The base footwear 101 comprises an upper 111 and a sole 112.

The sole 112 forms a pedestal between the foot and the ground. The sole 112 encloses the inferior surfaces of the foot. The sole 112 is described and defined elsewhere in this disclosure.

The upper 111 forms the superior structure of the base footwear 101. The upper 111 encloses the superior surfaces of the foot of the wearer. The upper 111 is described and defined elsewhere in this disclosure. The upper 111 comprises a vamp 131, a quarter 132, and a plurality of loop slits 133. The vamp 131 is the anterior portion of the upper 111 of the base footwear 101. The vamp 131 is defined elsewhere in this disclosure. The vamp 131 further comprises a tongue 151. The tongue 151 is described and defined elsewhere in this disclosure.

The quarter 132 is the posterior portion of the upper 111 of the base footwear 101. The quarter 132 is defined elsewhere in this disclosure. The quarter 132 further comprises a medial structure 161, a lateral structure 162, and a posterior structure 163. The medial structure 161 comprises the elements of the upper 111 that encloses the medial surfaces of the foot and ankle. The lateral structure 162 comprises the elements of the upper 111 that encloses the lateral surfaces of the foot and the ankle. The posterior structure 163 comprises the elements of the upper 111 that encloses the posterior surfaces of the foot and the ankle.

Each of the plurality of loop slits 133 is a slit that is formed through a surface selected from the vamp 131 and the quarter 132.

The ankle support structure 102 attaches to the base footwear 101. The ankle support structure 102 is a mechanical structure. The ankle support structure 102 attaches to the base footwear 101 such that the cant of the foot relative to the base footwear 101 is physically constrained. Specifically, the ankle support structure 102 physically limits the range of lateral rotation the ankle of the foot while the invention 100 is worn. The support provided by the ankle support structure 102 prevents injury to the ankle during rapid changes in direction. The ankle support structure 102 comprises a medial plate 121, a lateral plate 122, and a plurality of binding strips 123.

The medial plate 121 is a disk-shaped structure. The medial plate 121 has a rigid plate structure. The medial plate 121 attaches to the medial structure 161 of the quarter 132 of the upper 111 such that the medial plate 121 is positioned against the medial side of the ankle. The rigid structure of the medial plate 121 supports the ankle such that medial plate 121 prevents the ankle from laterally rotating in the medial direction.

The lateral plate 122 is a disk-shaped structure. The lateral plate 122 has a rigid plate structure. The lateral plate 122 attaches to the lateral structure 162 of the quarter 132 of the upper 111 such that the lateral plate 122 is positioned against the lateral side of the ankle. The rigid structure of the lateral plate 122 supports the ankle such that lateral plate 122 prevents the ankle from laterally rotating in the medial direction.

Each of the plurality of binding strips 123 is a webbing. Each of the plurality of binding strips 123 binds the medial plate 121 and the lateral plate 122 to the base footwear 101. The plurality of binding strips 123 further binds the medial plate 121 and the lateral plate 122 to the ankle. The plurality of binding strips 123 fixes the ankle support structure 102 to the ankle such that the position of the ankle is fixed relative to the ankle support structure 102. The plurality of binding strips 123 comprises a superior strap 141 and an inferior strap 142.

The superior strap 141 is a flexible textile structure. The superior strap 141 binds the ankle support structure 102 to the ankle such that the position of the ankle is fixed relative to the ankle support structure 102. The superior strap 141 comprises a superior webbing 171, a superior hook and loop fastener 172, and a superior seam 173.

The superior webbing 171 is a textile webbing structure. The superior webbing 171 is a flexible structure that comprises a tensile strength but no compressive strength. The superior webbing 171 binds the medial plate 121 and the lateral plate 122 to the ankle.

The superior hook and loop fastener 172 is a commercially available hook and loop fastener. The hook and loop fastener is defined elsewhere in this disclosure. The superior hook and loop fastener 172 attaches the superior webbing 171 to itself such that the superior webbing 171 forms a loop structure around the ankle. The superior hook and loop fastener 172 allows for the adjustment of the binding tension applied by the superior webbing 171 to the ankle, the medial plate 121, and the lateral plate 122.

The superior seam 173 is a sewn seam. The superior seam 173 permanently attaches the superior webbing 171 to the posterior structure 163 of the quarter 132 such that the superior webbing 171 can wrap around the ankle. The sewn seam is defined elsewhere in this disclosure.

The inferior strap 142 is a flexible textile structure. The inferior strap 142 binds the ankle support structure 102 to the ankle such that the position of the ankle is fixed relative to the ankle support structure 102. The inferior strap 142 further binds the ankle support structure 102 to the upper 111 of the base footwear 101. The inferior strap 142 attaches to the base footwear 101 at an inferior position relative to the superior strap 141. The inferior strap 142 comprises an inferior webbing 181 and an inferior hook and loop fastener 182.

The inferior webbing 181 is a textile webbing structure. The inferior webbing 181 is a flexible structure that comprises a tensile strength but no compressive strength. The inferior webbing 181 binds the medial plate 121 and the lateral plate 122 to the ankle. The inferior webbing 181 binds the medial plate 121 and the lateral plate 122 to the base footwear 101.

The inferior hook and loop fastener 182 is a commercially available hook and loop fastener. The hook and loop fastener is defined elsewhere in this disclosure. The inferior hook and loop fastener 182 attaches the inferior webbing 181 to itself such that the inferior webbing 181 forms a loop structure around the base footwear 101. The inferior hook and loop fastener 182 allows for the adjustment of the binding tension applied by the inferior webbing 181 to the foot, the medial plate 121 and the lateral plate 122. The inferior webbing 181 threads through each of the plurality of loop slits 133 such that the inferior webbing 181 attaches directly to the upper 111 of the base footwear 101. The tension applied by the inferior webbing 181 to the upper 111 of the base footwear 101 is adjustable using the inferior hook and loop fastener 182.

The inferior strap 142 inserts through each slit selected from the plurality of loop slits 133 such that the inferior strap 142 passes between the inferior side and the exterior side of the selected surface. The inferior strap 142 threads through each of the plurality of loop slits 133 such that the inferior strap 142 binds the ankle support structure 102 to the base footwear 101. The plurality of loop slits 133 threads through each of the plurality of loop slits 133 such that the inferior strap 142 binds the ankle support structure 102 to the ankle.

The plurality of loop slits 133 comprises a first loop slit 191, a second loop slit 192, a third loop slit 193, a fourth loop slit 194, a fifth loop slit 195, a sixth loop slit 196, a seventh loop slit 197, and an eighth loop slit 198.

The first loop slit 191 is a slit selected from the plurality of loop slits 133 that is formed through the lateral side of the vamp 131 of the upper 111. The inferior webbing 181 threads through the first loop slit 191 such that the inferior webbing 181 lays over the exterior surface of the tongue 151 of the vamp 131.

The second loop slit 192 is a slit selected from the plurality of loop slits 133 that is formed through the lateral structure 162 of the upper 111 of the ankle support structure 102. The inferior webbing 181 threads through the second loop slit 192 such that the inferior webbing 181 passes from the first loop slit 191 to the second loop slit 192 along the interior surface of the lateral structure 162.

The third loop slit 193 is a slit selected from the plurality of loop slits 133 that is formed through the lateral structure 162 of the upper 111 of the ankle support structure 102. The inferior webbing 181 threads through the third loop slit 193 such that the inferior webbing 181 passes from the second loop slit 192 to the third loop slit 193 along the exterior surface of the lateral structure 162.

The fourth loop slit 194 is a slit selected from the plurality of loop slits 133 that is formed through the posterior structure 163 of the upper 111 of the ankle support structure 102. The inferior webbing 181 threads through the fourth loop slit 194 such that the inferior webbing 181 passes from the third loop slit 193 to the fourth loop slit 194 along the interior surface of the lateral structure 162.

The fifth loop slit 195 is a slit selected from the plurality of loop slits 133 that is formed through the posterior structure 163 of the upper 111 of the ankle support structure 102. The inferior webbing 181 threads through the fifth loop slit 195 such that the inferior webbing 181 passes from the fourth loop slit 194 to the fifth loop slit 195 along the exterior surface of the lateral structure 162.

The sixth loop slit 196 is a slit selected from the plurality of loop slits 133 that is formed through the medial structure 161 of the upper 111 of the ankle support structure 102. The inferior webbing 181 threads through the sixth loop slit 196 such that the inferior webbing 181 passes from the fifth loop slit 195 to the sixth loop slit 196 along the interior surface of the lateral structure 162.

The seventh loop slit 197 is a slit selected from the plurality of loop slits 133 that is formed through the medial structure 161 of the upper 111 of the ankle support structure 102. The inferior webbing 181 threads through the seventh loop slit 197 such that the inferior webbing 181 passes from the sixth loop slit 196 to the seventh loop slit 197 along the exterior surface of the lateral structure 162.

The eighth loop slit 198 is a slit selected from the plurality of loop slits 133 that is formed through the lateral side of the vamp 131 of the upper 111. The inferior webbing 181 threads through the eighth loop slit 198 such that the inferior webbing 181 lays over the exterior surface of the tongue 151 of the vamp 131.

The sleeve structure 103 is a tubular textile structure. The sleeve structure 103 attaches to the top line of the base footwear 101 such that the foot inserts into the base footwear 101 by passing through the sleeve structure 103. The sleeve structure 103 forms a protective cushion that prevents the ankle support structure 102 from injuring the ankle.

The following definitions were used in this disclosure:

Ankle: As used in this disclosure, the ankle is the joint in the human body that joins the foot to the leg. The ankle comprises the lateral malleolus region of the fibula, the medial malleolus region of the tibia, and the talus. The talus attaches the lateral malleolus region of the fibula and the medial malleolus region of the tibia to the hindfoot region of the foot.

Anterior: As used in this disclosure, anterior is a term that is used to refer to the front side or direction of a structure. When comparing two objects, the anterior object is the object that is closer to the front of the structure.

Arch: As used in this disclosure, the arch refers to an arch formed in the foot proximal to the talus and metatarsal bones of the foot. The form of the arch helps to support and distribute the weight borne by the foot.

Athletic Footwear: As used in this disclosure, athletic footwear is a footwear item that is adapted for use by a person who is performing rapid foot movements requiring rapid changes of direction.

Ball of the Foot: As used in this disclosure, the ball of the foot is a padded area on the bottom of the foot of a person located between the toes and the arch of the foot. When the heel of the foot is raised, the ball of the foot supports the weight of the person.

Cord: As used in this disclosure, a cord is a long, thin, flexible, and prism shaped string, line, rope, or wire. Cords are made from yarns, piles, or strands of material that are braided or twisted together or from a monofilament (such as fishing line). Cords have tensile strength but are too flexible to provide compressive strength and are not suitable for use in pushing objects. String, line, cable, and rope are synonyms for cord.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Exterior: As used in this disclosure, the exterior is used as a relational term that implies that an object is not contained within the boundary of a structure or a space.

Feather: As used in this disclosure, the feather is the junction between the upper and the sole.

Flexible: As used in this disclosure, flexible refers to an object or material that will deform when a force is applied to it but that will not necessarily return to its original shape when the deforming force is removed.

Foot: As used in this disclosure, the foot refers to the portion of the leg that is below the ankle. Within this disclosure, the foot is further defined with a forefoot, a midfoot, a hindfoot, and a sole. The forefoot is the region of the foot is the anterior portion of the foot within which the phalanges and the metatarsals bones are located. The midfoot is the region of the foot within which the navicular, cuboid, and cuneiform bones are located. The hindfoot is the region of the foot that is posterior to the midfoot. The sole refers to the inferior surfaces of the foot located underneath the forefoot, the midfoot, and the hindfoot. The health foot further comprises five toes formed at the distal end of the forefoot.

Footwear: As used in this disclosure, footwear refers to a protective structure that is worn on a foot. Footwear is commonly referred to as a shoe.

Frenulum: As used in this disclosure, the frenulum is the junction between the tongue and the upper where the tongue is connected to the upper.

Ground: As used in this disclosure, the ground is a solid supporting surface formed by the Earth. The term level ground means that the supporting surface formed by the ground is roughly perpendicular to the force of gravity. Always use supporting surface.

Heel: As used in this disclosure, the heel is the portion of the sole or the outsole that is underneath the ankle and posterior to the arch of the foot of the wearer.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook/loop surface" with the understanding that when the two objects are fastened together one of the two objects will have a hook surface and the remaining object will have the loop surface.

Inferior: As used in this disclosure, the term inferior refers to a directional reference that is parallel to and in the same direction as the force of gravity when an object is positioned or used normally.

Insert: As used in this disclosure, an insert is an orthotic cushion that inserts into footwear such that the insert rests on the insole of the footwear. The insert forms a structure between the foot and the insole.

Insole: As used in this disclosure, the insole is the component of a shoe sole that is proximal to the wearer's foot.

Interior: As used in this disclosure, the interior is used as a relational term that implies that an object is contained within the boundary of a structure or a space.

Lateral: As used in this disclosure, lateral refers to a directional sense or location of the body. Specifically, lateral refers to an object or a side of an object that is proximal to the side or that is distal from the medial axis of the body.

Medial: As used in this disclosure, medial refers to a directional sense or location of the body. Specifically, medial refers to a first object or a side of a first object that is closer to the medial axis or more distal from the side of the body relative to a second object or side of a second object.

Outsole: As used in this disclosure, the outsole is the outer component of the sole of the shoe that is in contact with the ground.

Pedestal: As used in this disclosure, a pedestal is an intermediary load bearing structure that forms a load path between a supporting surface and an object, structure, or load.

Plate: As used in this disclosure, a plate is a smooth, flat and semi-rigid or rigid structure that has at least one dimension that: a) is of uniform thickness; and b) that appears thin relative to the other dimensions of the object. Plates often have a rectangular appearance. Plates often have a disk-like structure. The face of the plate is a surface of the plate selected from the group consisting of: a) the surface of the plate with the greatest surface area; b) the surface of the plate that is distal from the surface of the plate with the greatest surface area. The edges of the plate comprises the surfaces of the plate that would not be considered faces as defined above. As defined in this disclosure, plates may be made of any material, but are commonly made of metal, plastic, and wood. When made of wood, a plate is often referred to as a board or a plank.

Posterior: As used in this disclosure, posterior is a term that is used to refer to the side of an object that is distal or in the opposite direction of the anterior side. When comparing two items, the posterior item is the item that is distal from the anterior of the object.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Quarter: As used in this disclosure, the quarter is the portion of the upper that is connected to the vamp and that surrounds the heel and the sides of the foot.

Raw Edge: As used in this disclosure, a raw edge refers to one of two edges that are formed when a slit is cut through the face of the sheeting. The one or more ends of the slit are called the termination points.

Rigid Structure: As used in this disclosure, a rigid structure is a solid structure formed from an inelastic material that resists changes in shape. A rigid structure will permanently deform as it fails under a force.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, a laser seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Shoe: As used in this disclosure, shoe is a synonym for footwear that excludes open footwear with a primarily open upper such as sandals and flip flops.

Shoe Lace: As used in this disclosure, a shoe lace is a cord used to tighten footwear while the footwear is worn.

Sleeve: As used in this disclosure, a sleeve is a tube like covering that is placed over a rod, shaft or other cylindrical object.

Slit: As used in this disclosure, a slit is a long narrow cut or opening that is formed in or through an object.

Sole: As used in this disclosure, the sole component of a shoe that forms the undersurface of the shoe and comes in contact with the ground.

Strap: As used in this disclosure, a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Superior: As used in this disclosure, the term superior refers to a directional reference that is parallel to and in the opposite direction of the force of gravity when an object is positioned or used normally.

Supporting Surface: As used in this disclosure, a supporting surface is a horizontal surface upon which an object is placed and to which the load path of the object is transferred. This disclosure assumes that an object placed on the supporting surface is in an orientation that is appropriate for the normal or anticipated use of the object.

Textile: As used in this disclosure, a textile is a material that is woven, knitted, braided or felted. Synonyms in common usage for this definition include fabric and cloth. The two surfaces of the textile with the greatest surface area are called the faces of the textile.

Thread: As used in this disclosure, to thread is a verb that refers to inserting a cord or a webbing through one or more holes.

Toe: As used in this disclosure, the toe is a digit on the distal end of a foot. The toes are formed by the phalanges of the foot.

Tongue: As used in this disclosure, the tongue is the portion a shoe that is attached to the vamp such that the tongue sits underneath the upper and underneath the fastener (such as shoelaces) used to tighten the shoe.

Top Line: As used in this disclosure, the top line is the superior edge of the upper. The foot is generally inserted into an upper at the top line. The top line is often referred to as the collar.

Tube: As used in this disclosure, the term tube is used to describe a rigid hollow prism-shaped device with two open ends. While tubes that are suitable for use in this disclosure are often used to transport or conveys fluids or gases, the purpose of the tubes in this disclosure are structural. In this disclosure, the terms inner dimension and outer dimension of a tube are used as they would be used by those skilled in the plumbing arts.

Tubular Textile: As used in this disclosure, a tubular textile is a textile that is woven, knitted, or braided into a seamless tube like shape.

Upper: As used in this disclosure, the upper is the portion of the shoe that is superior to the sole.

Vamp: As used in this disclosure, the vamp is the portion of the upper that covers the superior portion of the foot from the toes to where the vamp connects to the quarter.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects. The shape of a webbing is approximated by a disk shape. The two surfaces of a webbing with the greatest surface area are called the faces of the webbing.

Welt: As used in this disclosure, a welt is a piece of material that reinforces the attachment of the upper to the sole.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. An athletic shoe having integral ankle support comprising
    a base footwear, an ankle support structure, and a sleeve structure;
    wherein the ankle support structure and the sleeve structure attach to the base footwear;
    wherein the athletic shoe having integral ankle support is an item of footwear;
    wherein the athletic shoe having integral ankle support is adapted for use with a foot;
    wherein the athletic shoe having integral ankle support prevents an ankle to form a cant in the athletic shoe having integral ankle support;
    wherein the ankle support structure comprises a medial plate, a lateral plate, and a plurality of binding strips;
    wherein the upper comprises a vamp, a quarter, and a plurality of loop slits;
    wherein the quarter further comprises a medial structure, a lateral structure, and a posterior structure;
    wherein the plurality of loop slits comprises a first loop slit, a second loop slit, a third loop slit, a fourth loop slit, a fifth loop slit, a sixth loop slit, a seventh loop slit, and an eighth loop slit.

2. The athletic shoe having integral ankle support according to claim 1
    wherein the sleeve structure is a tubular textile structure;
    wherein the sleeve structure attaches to the base footwear such that the foot inserts into the base footwear by passing through the sleeve structure;
    wherein the base footwear is a shoe.

3. The athletic shoe having integral ankle support according to claim 2
    wherein the ankle support structure is a mechanical structure;
    wherein the ankle support structure attaches to the base footwear such that the cant of the foot relative to the base footwear is physically constrained;
    wherein the ankle support structure physically limits the range of lateral rotation the ankle.

4. The athletic shoe having integral ankle support according to claim 3
    wherein the base footwear comprises an upper and a sole;

wherein the sole forms a pedestal between the foot and the ground;

wherein the sole encloses the inferior surfaces of the foot;

wherein the upper forms the superior structure of the base footwear;

wherein the upper encloses the superior surfaces of the foot of the wearer.

5. The athletic shoe having integral ankle support according to claim 4 wherein the vamp is the anterior portion of the upper of the base footwear;

wherein the quarter is the posterior portion of the upper of the base footwear;

wherein each of the plurality of loop slits is a slit that is formed through a surface selected from the vamp and the quarter;

wherein the vamp further comprises a tongue.

6. The athletic shoe having integral ankle support according to claim 5 wherein the medial structure comprises elements of the upper that encloses the medial surfaces of the foot and ankle;

wherein the lateral structure comprises elements of the upper that encloses the lateral surfaces of the foot and the ankle;

wherein the posterior structure comprises elements of the upper that encloses the posterior surfaces of the foot and the ankle.

7. The athletic shoe having integral ankle support according to claim 6 wherein the medial plate is a rigid disk-shaped structure;

wherein the medial plate attaches to the medial structure of the quarter of the upper such that the medial plate is positioned against the medial side of the ankle;

wherein the rigid structure of the medial plate supports the ankle such that the medial plate prevents the ankle from laterally rotating in the medial direction.

8. The athletic shoe having integral ankle support according to claim 7 wherein the lateral plate is a rigid disk-shaped structure;

wherein the lateral plate attaches to the lateral structure of the quarter of the upper such that the lateral plate is positioned against the lateral side of the ankle;

wherein the rigid structure of the lateral plate supports the ankle such that the lateral plate prevents the ankle from laterally rotating in the medial direction.

9. The athletic shoe having integral ankle support according to claim 8 wherein each of the plurality of binding strips is a webbing;

wherein the plurality of binding strips further binds the medial plate and the lateral plate to the ankle;

wherein the plurality of binding strips fixes the ankle support structure to the ankle such that the position of the ankle is fixed relative to the ankle support structure.

10. The athletic shoe having integral ankle support according to claim 9 wherein the plurality of binding strips comprises a superior strap and an inferior strap;

wherein the superior strap is a flexible textile structure;

wherein the superior strap binds the ankle support structure to the ankle such that the position of the ankle is fixed relative to the ankle support structure;

wherein the inferior strap is a flexible textile structure;

wherein the inferior strap binds the ankle support structure to the ankle such that the position of the ankle is fixed relative to the ankle support structure;

wherein the inferior strap further binds the ankle support structure to the upper of the base footwear.

11. The athletic shoe having integral ankle support according to claim 10 wherein the inferior strap attaches to the base footwear at an inferior position relative to the superior strap.

12. The athletic shoe having integral ankle support according to claim 11 wherein the superior strap comprises a superior webbing, a superior hook and loop fastener, and a superior seam;

wherein the superior webbing binds the medial plate and the lateral plate to the ankle;

wherein the superior hook and loop fastener attaches the superior webbing to itself;

wherein the superior seam permanently attaches the superior webbing to the posterior structure of the quarter.

13. The athletic shoe having integral ankle support according to claim 12 wherein the superior webbing is a textile webbing structure.

14. The athletic shoe having integral ankle support according to claim 13 wherein the superior hook and loop fastener attaches the superior webbing to itself such that the superior webbing forms a loop structure around the ankle;

wherein the superior hook and loop fastener allows for the adjustment of the binding tension applied by the superior webbing to the ankle, the medial plate, and the lateral plate.

15. The athletic shoe having integral ankle support according to claim 14 wherein the superior seam is a sewn seam.

16. The athletic shoe having integral ankle support according to claim 15 wherein the inferior strap comprises an inferior webbing and an inferior hook and loop fastener;

wherein the inferior webbing binds the medial plate and the lateral plate to the ankle;

wherein the inferior webbing binds the medial plate and the lateral plate to the base footwear;

wherein the inferior hook and loop fastener attaches the inferior webbing to itself.

17. The athletic shoe having integral ankle support according to claim 16 wherein the inferior webbing is a textile webbing structure;

wherein the inferior hook and loop fastener attaches the inferior webbing to itself such that the inferior webbing forms a loop structure around the base footwear;

wherein the inferior hook and loop fastener allows for the adjustment of the binding tension applied by the inferior webbing to the foot, the medial plate and the lateral plate.

18. The athletic shoe having integral ankle support according to claim 17 wherein the inferior webbing threads through each of the plurality of loop slits such that the inferior webbing attaches directly to the upper of the base footwear;

wherein the inferior strap inserts through each slit selected from the plurality of loop slits such that the inferior strap passes between the inferior side and the exterior side of the selected surface.

19. The athletic shoe having integral ankle support according to claim 18;

wherein the first loop slit is a slit selected from the plurality of loop slits that is formed through the lateral side of the vamp of the upper;

wherein the inferior webbing threads through the first loop slit such that the inferior webbing lays over the exterior surface of the tongue of the vamp;

wherein the second loop slit is a slit selected from the plurality of loop slits that is formed through the lateral structure of the upper of the ankle support structure;

wherein the inferior webbing threads through the second loop slit such that the inferior webbing passes from the first loop slit to the second loop slit along the interior surface of the lateral structure;

wherein the third loop slit is a slit selected from the plurality of loop slits that is formed through the lateral structure of the upper of the ankle support structure;

wherein the inferior webbing threads through the third loop slit such that the inferior webbing passes from the second loop slit to the third loop slit along the exterior surface of the lateral structure;

wherein the fourth loop slit is a slit selected from the plurality of loop slits that is formed through the posterior structure of the upper of the ankle support structure;

wherein the inferior webbing threads through the fourth loop slit such that the inferior webbing passes from the third loop slit to the fourth loop slit along the interior surface of the lateral structure;

wherein the fifth loop slit is a slit selected from the plurality of loop slits that is formed through the posterior structure of the upper of the ankle support structure;

wherein the inferior webbing threads through the fifth loop slit such that the inferior webbing passes from the fourth loop slit to the fifth loop slit along the exterior surface of the lateral structure;

wherein the sixth loop slit is a slit selected from the plurality of loop slits that is formed through the medial structure of the upper of the ankle support structure;

wherein the inferior webbing threads through the sixth loop slit such that the inferior webbing passes from the fifth loop slit to the sixth loop slit along the interior surface of the lateral structure;

wherein the seventh loop slit is a slit selected from the plurality of loop slits that is formed through the medial structure of the upper of the ankle support structure;

wherein the inferior webbing threads through the seventh loop slit such that the inferior webbing passes from the sixth loop slit to the seventh loop slit along the exterior surface of the lateral structure;

wherein the eighth loop slit is a slit selected from the plurality of loop slits that is formed through the lateral side of the vamp of the upper;

wherein the inferior webbing threads through the eighth loop slit such that the inferior webbing lays over the exterior surface of the tongue of the vamp.

\* \* \* \* \*